US012508190B2

(12) United States Patent
Liu et al.

(10) Patent No.: US 12,508,190 B2
(45) Date of Patent: Dec. 30, 2025

(54) NEGATIVE-PRESSURE MASSAGING DEVICE

(71) Applicants: BIBOTING INTERNATIONAL CO., LTD., Taoyuan (TW); Po-Chang Liu, Taoyuan (TW)

(72) Inventors: Po-Chang Liu, Taoyuan (TW); Chia-Hsueh Hsieh, Taoyuan (TW)

(73) Assignees: BIBOTING INTERNATIONAL CO., LTD., Taoyuan (TW); Po-Chang Liu, Taoyuan (TW)

(*) Notice: Subject to any disclaimer, the term of this patent is extended or adjusted under 35 U.S.C. 154(b) by 985 days.

(21) Appl. No.: 17/676,784

(22) Filed: Feb. 21, 2022

(65) Prior Publication Data

US 2023/0263699 A1 Aug. 24, 2023

(51) Int. Cl.

*A61H 9/00* (2006.01)
*A61H 39/06* (2006.01)
*A61M 21/00* (2006.01)
*A61M 21/02* (2006.01)

(52) U.S. Cl.

CPC .......... *A61H 9/0057* (2013.01); *A61M 21/02* (2013.01); *A61H 2009/0064* (2013.01); *A61H 2201/0207* (2013.01); *A61H 2201/0221* (2013.01); *A61H 2201/102* (2013.01); *A61H 2201/5082* (2013.01); *A61M 2021/0016* (2013.01); *A61M 2205/3368* (2013.01); *A61M 2205/36* (2013.01)

(58) Field of Classification Search

CPC .......... A61H 9/0057; A61H 2009/0064; A61H 2201/0207; A61H 2201/0221; A61H 2201/102; A61H 2201/5082; A61H 39/06; A61M 21/02; A61M 2021/0016; A61M 2205/3368; A61M 2205/36; A61M 2021/0022; A61M 2021/0044

See application file for complete search history.

(56) References Cited

U.S. PATENT DOCUMENTS

| | | | | | |
|---|---|---|---|---|---|
| 2008/0065176 | A1* | 3/2008 | Zhang | A61N 1/44 | 607/88 |
| 2010/0137256 | A1* | 6/2010 | Haddad | A61M 1/08 | 604/315 |
| 2014/0236072 | A1* | 8/2014 | Zhang | A61M 1/06 | 604/23 |

FOREIGN PATENT DOCUMENTS

| | | | | | |
|---|---|---|---|---|---|
| CN | 206167649 | U | * | 5/2017 | |
| CN | 109289306 | A | * | 2/2019 | B01D 35/306 |
| CN | 110025462 | A | * | 7/2019 | A61N 1/18 |

(Continued)

*Primary Examiner* — Carrie R Dorna
*Assistant Examiner* — Joshua Daryl D Lannu
(74) *Attorney, Agent, or Firm* — HDLS IPR SERVICES; Chun-Ming Shih

(57) ABSTRACT

A negative-pressure massaging device capable of volatilizing essential oil is provided. The negative-pressure massaging device includes a negative-pressure cup and an essential oil volatilizing structure. The essential oil volatilizing structure is disposed in the negative-pressure cup and includes a heat conducting unit, a heating unit, and an essential oil unit. The heating unit is disposed on and contacts the heat conducting unit to heat the heat conducting unit. The essential oil unit is disposed on and contacts the heat conducting unit to be heated. The essential oil unit is heated by the heat conducting unit to volatilize essential oil into the negative-pressure cup. Accordingly, an aromatherapy may be provided when a negative-pressure massaging treatment is performed.

13 Claims, 8 Drawing Sheets

(56) References Cited

FOREIGN PATENT DOCUMENTS

CN 211326651 U * 8/2020

* cited by examiner

NEGATIVE-PRESSURE MASSAGING DEVICE

BACKGROUND OF THE DISCLOSURE

Technical Field

The present disclosure relates to a negative-pressure massage, particularly to a negative-pressure massaging device capable of volatilizing essential oil.

Description of Related Art

A related-art negative-pressure massaging device is to suck air in a negative-pressure cup to form a negative-pressure status in the negative-pressure cup, thus a surface at an uncomfortable part of a person needing the massage is formed with a protruding portion to achieve a massaging effect.

The protruding portion on the surface of the person, which is to be negative-pressure massaged, is formed via the negative-pressure generated by the negative-pressure massaging device. However, a circular blood stasis part is formed because of the protruding portion, the blood stasis part would require a period of time (for example several days to one week) to recover, and the person having the massage often has the circular blood stasis part on his/her body for several days to one week.

The applicant of the present disclosure has provided an idea of introducing an aromatherapy to the related-art negative-pressure massaging device, as such, the essential oil may be penetrated into the circular blood stasis part to relief the uncomfortable feelings caused by the circular blood stasis part and make the circular blood stasis part be recovered within a shorter time.

However, the related-art negative-pressure massaging device is not provided with an aromatherapy effect, the applicant of the present disclosure has devoted himself for improving the mentioned disadvantages.

SUMMARY OF THE DISCLOSURE

The present disclosure is to provide a negative-pressure massaging device capable of volatilizing essential oil, in which an essential oil volatilizing structure is disposed in a negative-pressure cup, thus an aromatherapy is provided when a negative-pressure massaging treatment is performed.

The present disclosure is to provide a negative-pressure massaging device capable of volatilizing essential oil, which includes an air permeable cover capable of being easily detached, an essential oil unit capable of being easily replenished or replaced and a heat conducting unit having an anti-rotating function relative to the air permeable cover.

Accordingly, the present disclosure provides a negative-pressure massaging device capable of volatilizing essential oil, which includes a negative-pressure cup and an essential oil volatilizing structure. The essential oil volatilizing structure is disposed in the negative-pressure cup and includes a heat conducting unit: a heating unit, disposed on and contacting the heat conducting unit to heat the heat conducting unit; and an essential oil unit, disposed on and contacting the heat conducting unit to be heated. The essential oil unit is heated by the heat conducting unit to volatilize essential oil into the negative-pressure cup.

Advantages achieved by the present disclosure are as follows. The aromatherapy may be provided when the negative-pressure massaging treatment is performed. The present disclosure further has an air permeable cover capable of being easily detached, the essential oil unit capable of being easily replenished or replaced and the heat conducting unit with an anti-rotating function relative to the air permeable cover.

BRIEF DESCRIPTION OF THE DRAWINGS

The features of the disclosure believed to be novel are set forth with particularity in the appended claims. The disclosure itself, however, may be best understood by reference to the following detailed description of the disclosure, which describes a number of exemplary embodiments of the disclosure, taken in conjunction with the accompanying drawings, in which:

DETAILED DESCRIPTION OF THE DISCLOSURE

The technical contents of this disclosure will become apparent with the detailed description of embodiments accompanied with the illustration of related drawings as follows. It is intended that the embodiments and drawings disclosed herein are to be considered illustrative rather than restrictive.

Figure 6:
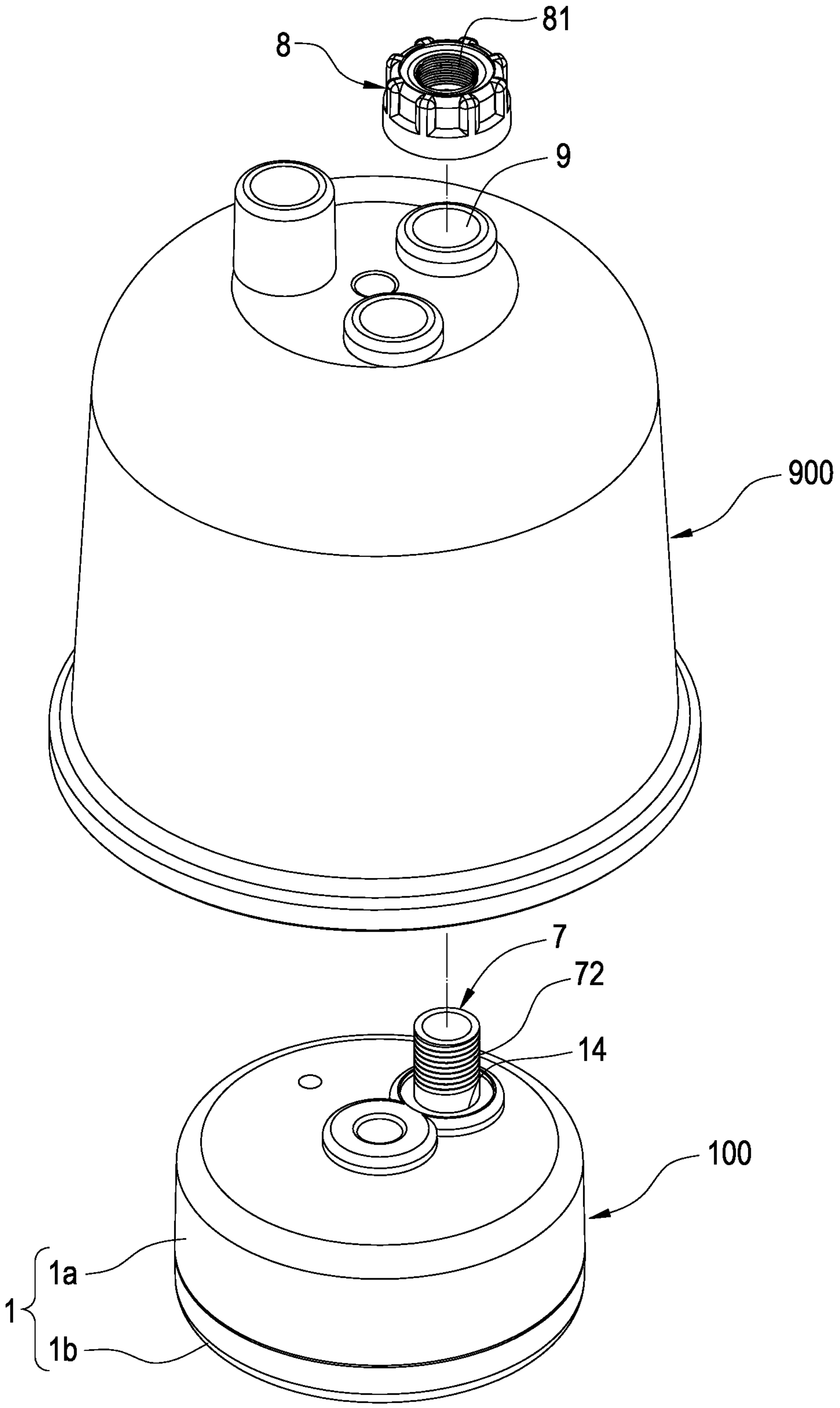
FIG. 6 is a perspective exploded view showing the negative-pressure massaging device and the essential oil volatilizing structure before being assembled according to the present disclosure.

Please refer to FIG. 6, the present disclosure provides a negative-pressure massaging device capable of volatilizing essential oil. The negative-pressure massaging device includes an essential oil volatilizing structure 100 and a negative-pressure cup 900, and is used for performing an aromatherapy to an uncomfortable part of a person when the person is having a massaging treatment. The essential oil volatilizing structure 100 is disposed in the negative-pressure cup 900.

Please refer from FIG. 1 to FIG. 4, the essential oil volatilizing structure 100 mainly includes a heat conducting unit 2, a heating unit 3 and an essential oil unit 4. In some embodiments, the essential oil volatilizing structure 100 further includes a housing 1 and an electric circuit board 5.

In some embodiments, the essential oil volatilizing structure 100 further includes a fastening column 7 and a fastening unit 8.

Figure 2:
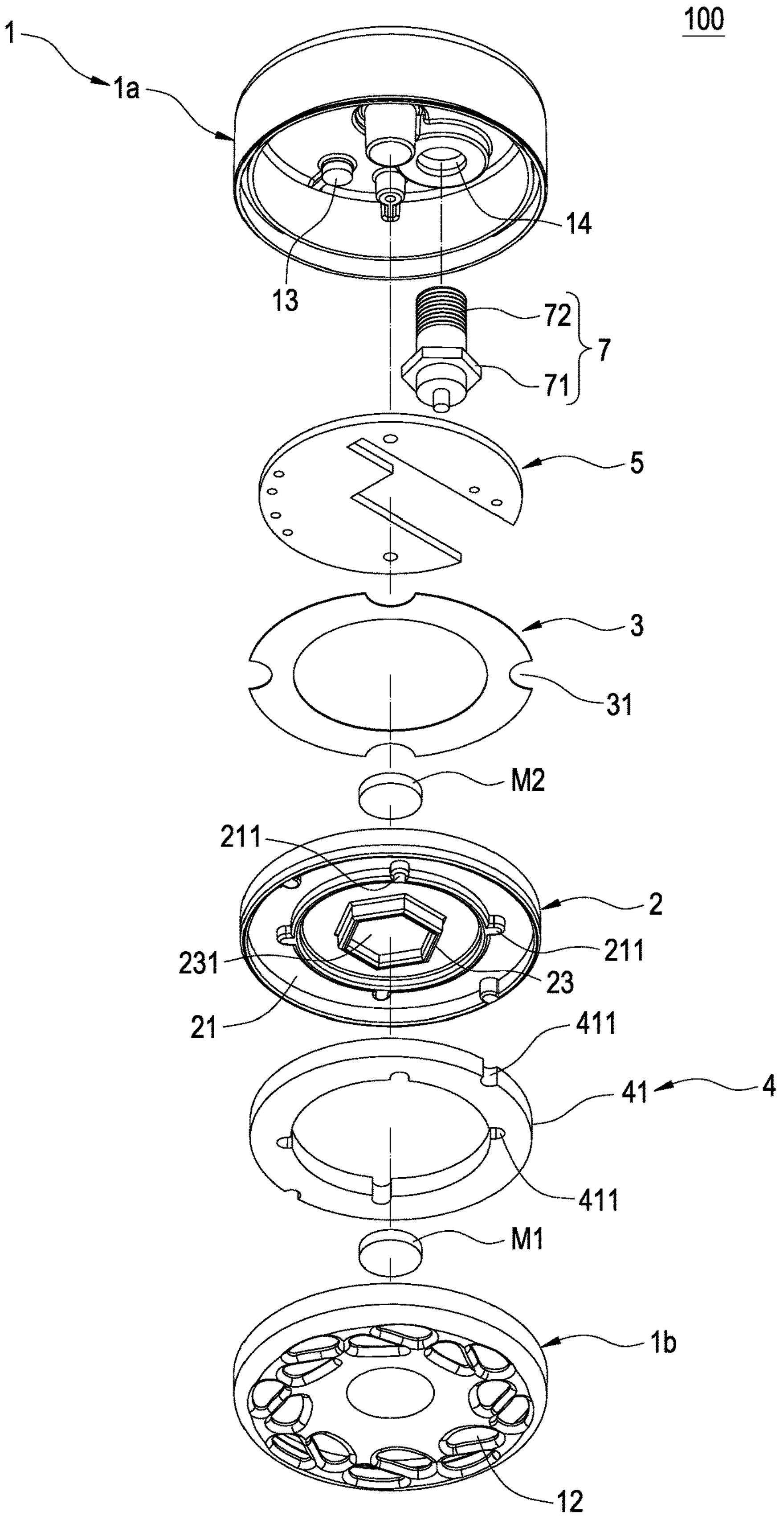
FIG. 2 is a perspective exploded view showing the essential oil volatilizing structure from an upward view according to the present disclosure.
Figure 3:
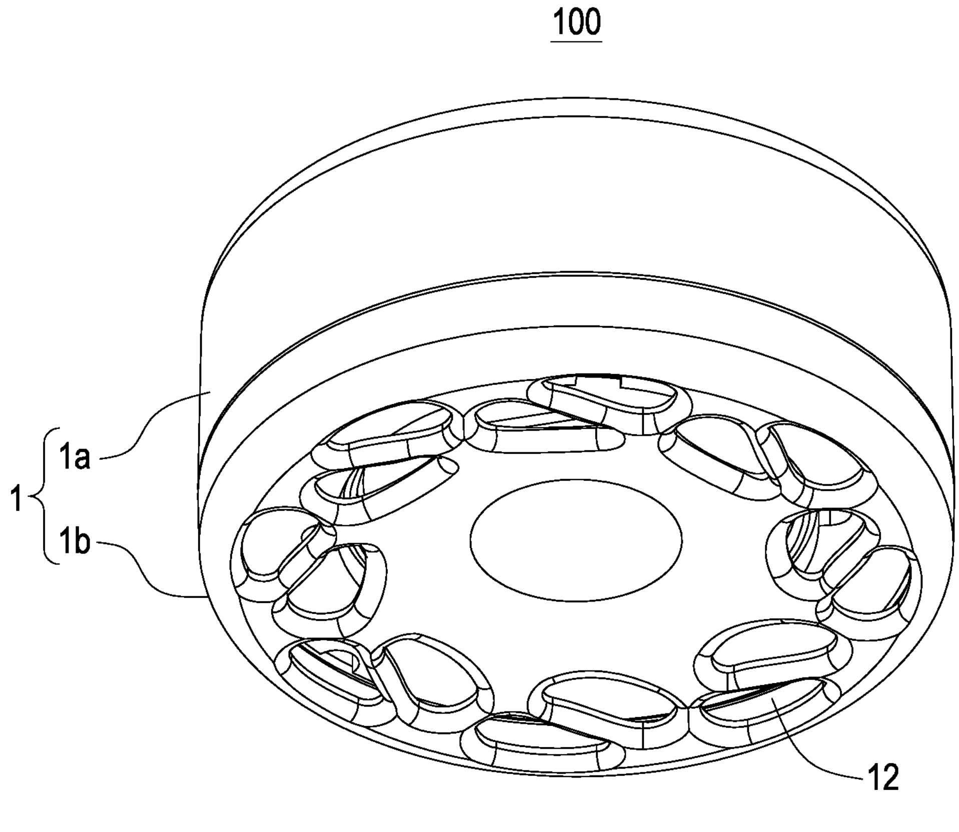
FIG. 3 is a perspective view showing the assembly of the essential oil volatilizing structure of FIG. 2 according to the present disclosure.
Figure 5:
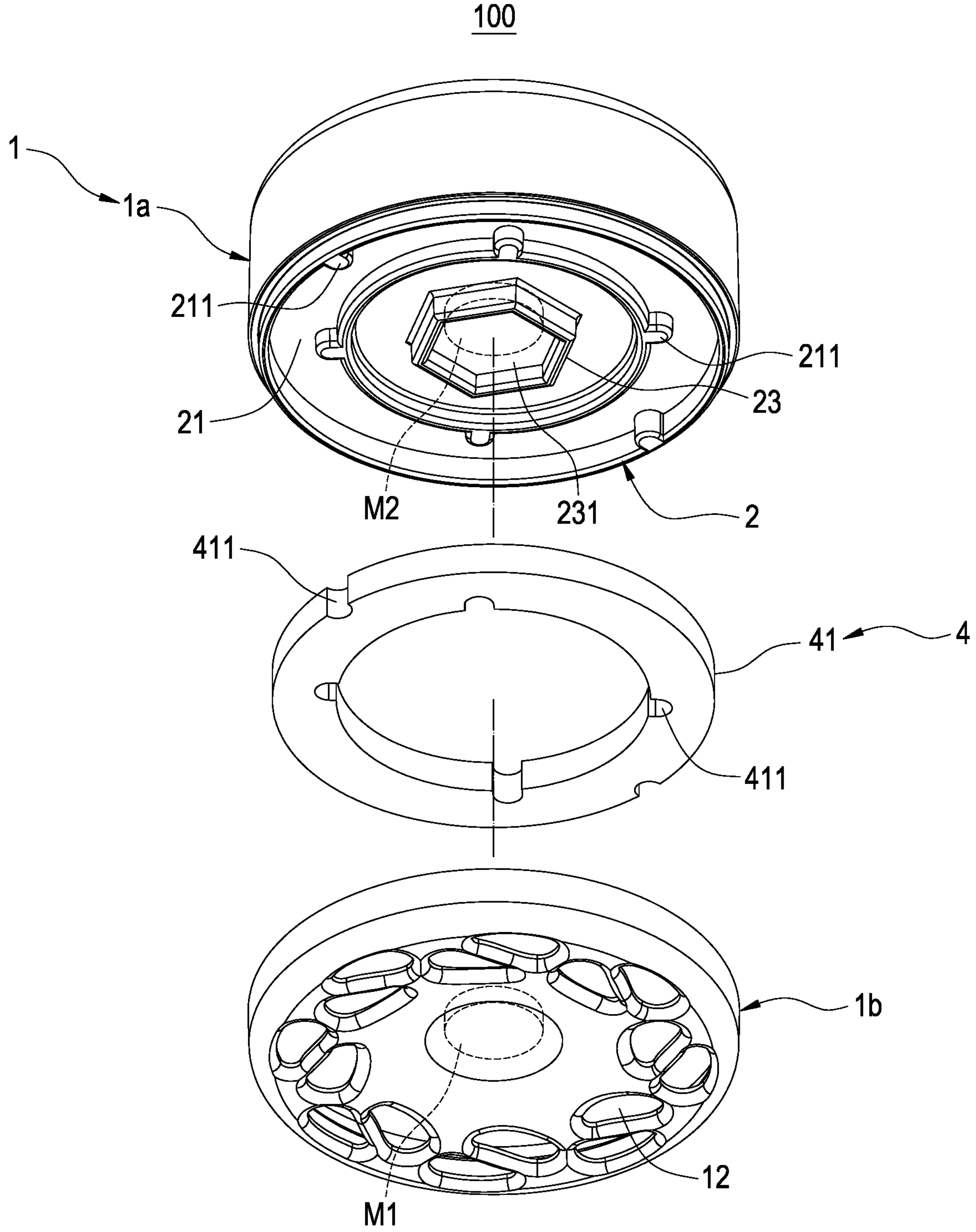
FIG. 5 is a perspective view showing the essential oil volatilizing structure with the housing being detached according to the present disclosure.

The housing 1 has a seat member 1*a* and an air permeable cover 1*b* capable of being mutually assembled. As shown in FIG. 2, the seat member 1*a* has a seat opening (not labeled), and the electric circuit board 5 is fastened on the seat member 1*a*. Please refer to FIG. 5, the heat conducting unit 2 covers the seat member 1*a* corresponding to a location of the seat opening to be mutually fastened, thus the electric circuit board 5 is sealed between the seat member 1*a* and the heat conducting unit 2. The air permeable cover 1*b* detachably covers the seat member 1*a* corresponding to the location of the seat opening (or corresponding to the heat conducting unit 2), thus the heat conducting unit 2 is covered in the housing 1, and the air permeable cover 1*b* has a plurality of (equal to or more than two) air holes 12.

The heat conducting unit 2 may be any member capable of conducting heat, for example a metal member or a non-metal member, but here is not intended to be limiting. As shown in figures, the heat conducting unit 2 has an inner surface and an outer surface facing each other and are not labeled.

The heating unit 3 is disposed on the inner surface of the heat conducting unit 2, and the heating unit 3 contacts the inner surface of the heat conducting unit 2 to transfer heat. The electric circuit board 5 is electrically connected to the heating unit 3 to control a heating operation provided by the heating unit 3 to the heat conducting unit 2.

The essential oil unit 4 may be any member allowing an essential oil to be volatilized through being heated, for example a solid-state essential oil (for example an essential oil paste or an essential oil piece, not shown in figures), or a member as shown in figures including a liquid-state essential oil (not shown in figures) and an essential oil carrying member 41. In some embodiments, the member including the liquid-state essential oil and the essential oil carrying member 41 are used as an example for illustrations. The essential oil carrying member 41 may be any member allowing the essential oil to be absorbed. In some embodiments and as shown in figures, a cotton member is used as an example for illustrations. The essential oil unit 4 may be formed through a user making the cotton member absorb the liquid-state essential oil or dropping the essential oil on the cotton member.

The essential oil unit 4 is disposed on the outer surface of the heat conducting unit 2, and the essential oil unit 4 contacts the outer surface of the heat conducting unit 2 to be heated.

Figure 4:
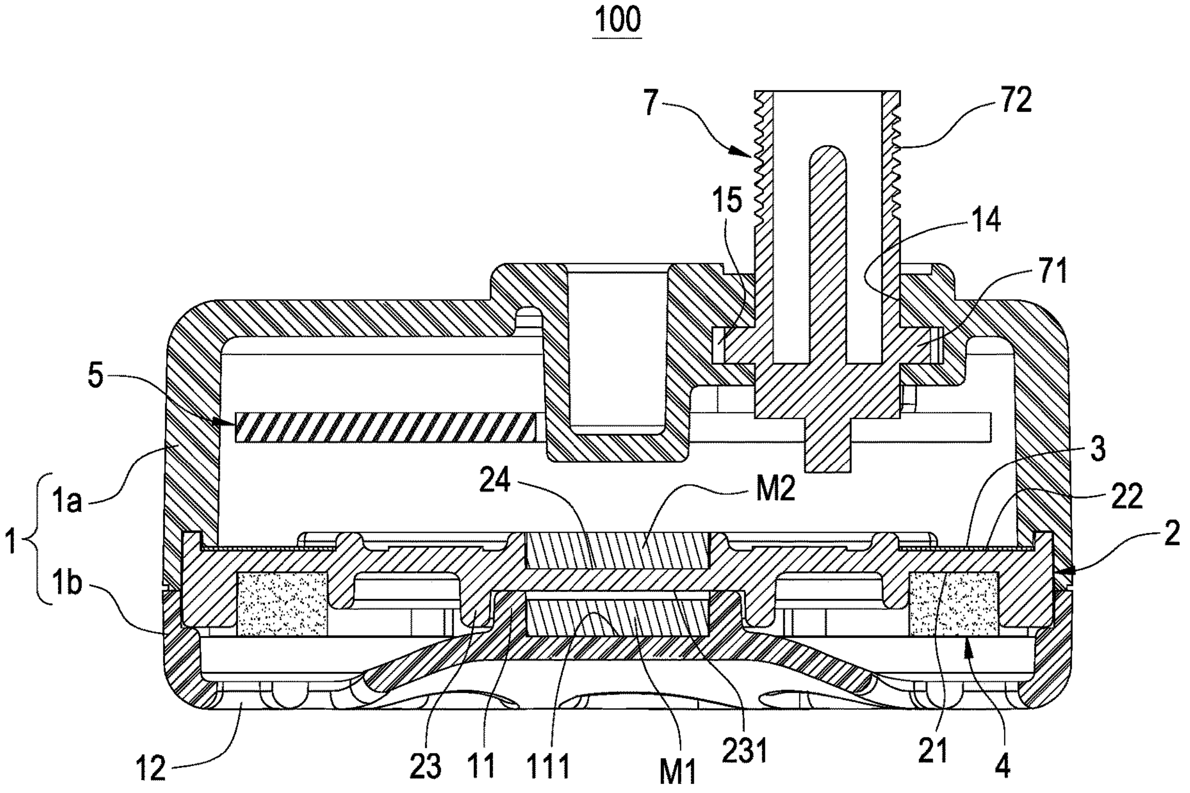
FIG. 4 is a cross sectional view showing the essential oil volatilizing structure of FIG. 3 according to the present disclosure.
Figure 7:
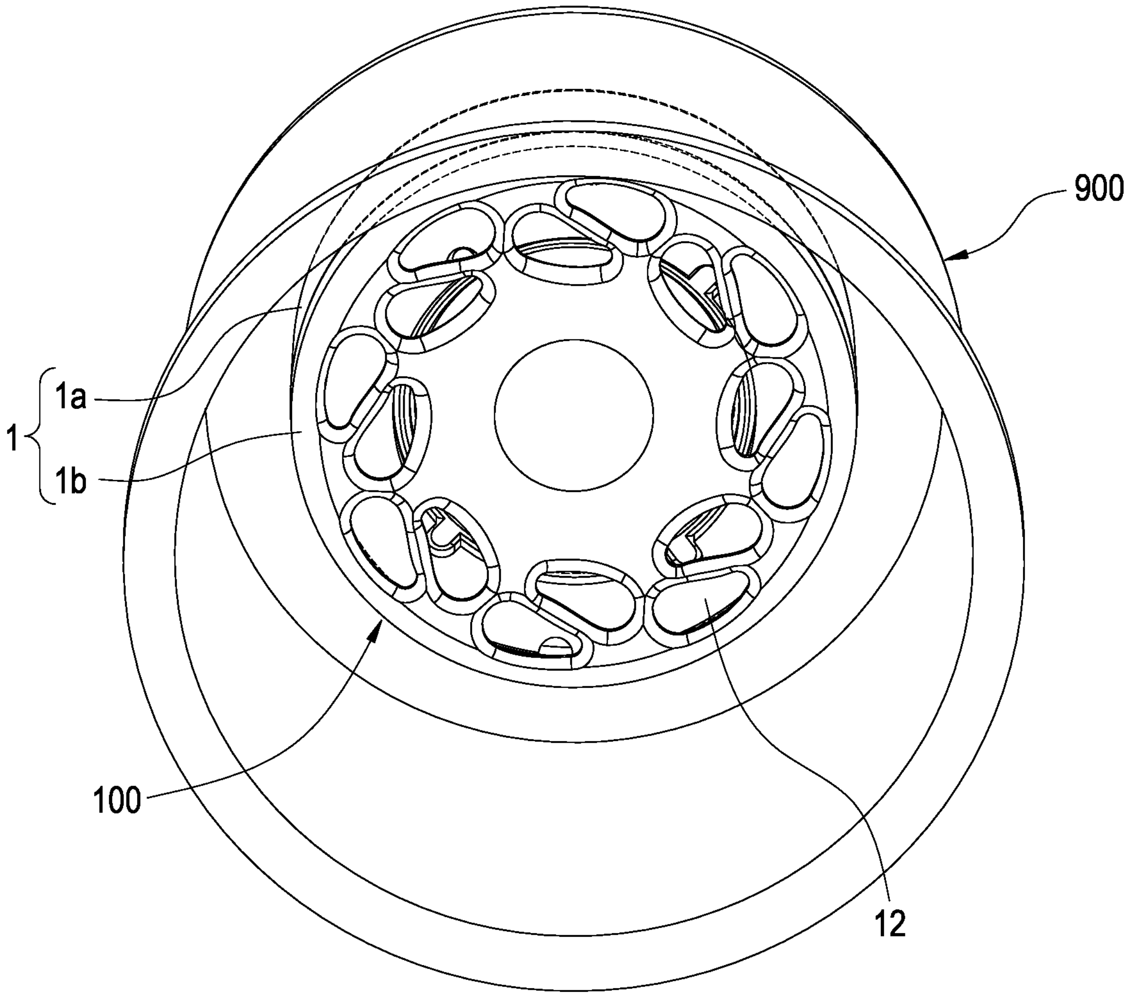
FIG. 7 is a perspective view showing the assembly of the negative-pressure massaging device and the essential oil volatilizing structure after being assembled according to the present disclosure.
Figure 8:
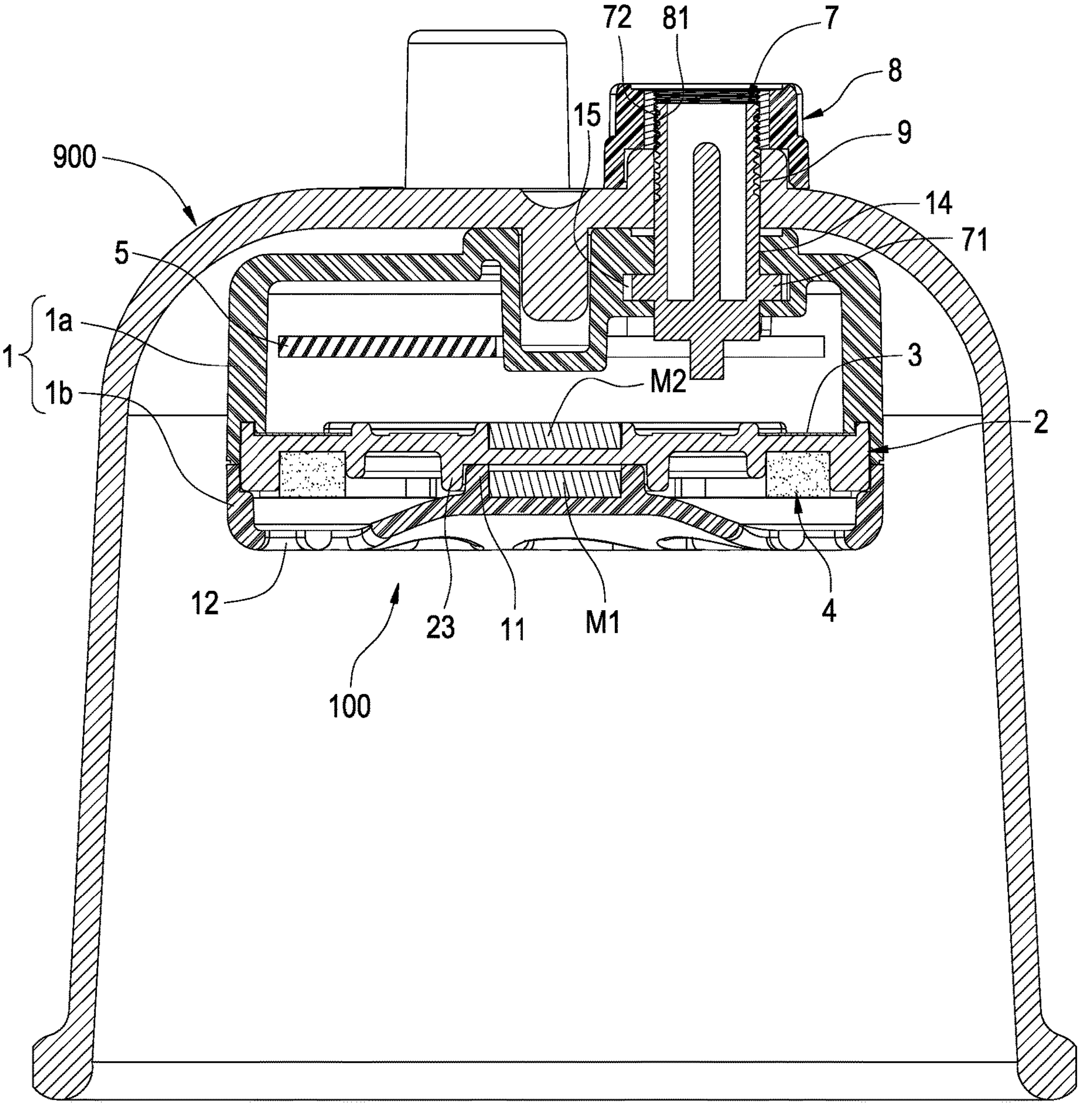
FIG. 8 is a cross sectional view showing the negative-pressure massaging device of FIG. 7 according to the present disclosure.

Please refer to FIG. 4, FIG. 7 and FIG. 8, when the user uses the negative-pressure cup 900 to massage the uncomfortable part, the heating unit 3 is controlled to heat the heat conducting unit 2 to make the heat of the heat conducting unit 2 be transferred to the essential oil unit 4, the liquid-state essential oil absorbed in the essential oil carrying member 41 is volatized to the negative-pressure cup 900 through the air holes 12 to perform an aromatherapy to the uncomfortable part, thus the volatized essential oil penetrates into deep tissues through the skins to achieve effects of massage and aromatherapy.

Figure 1:
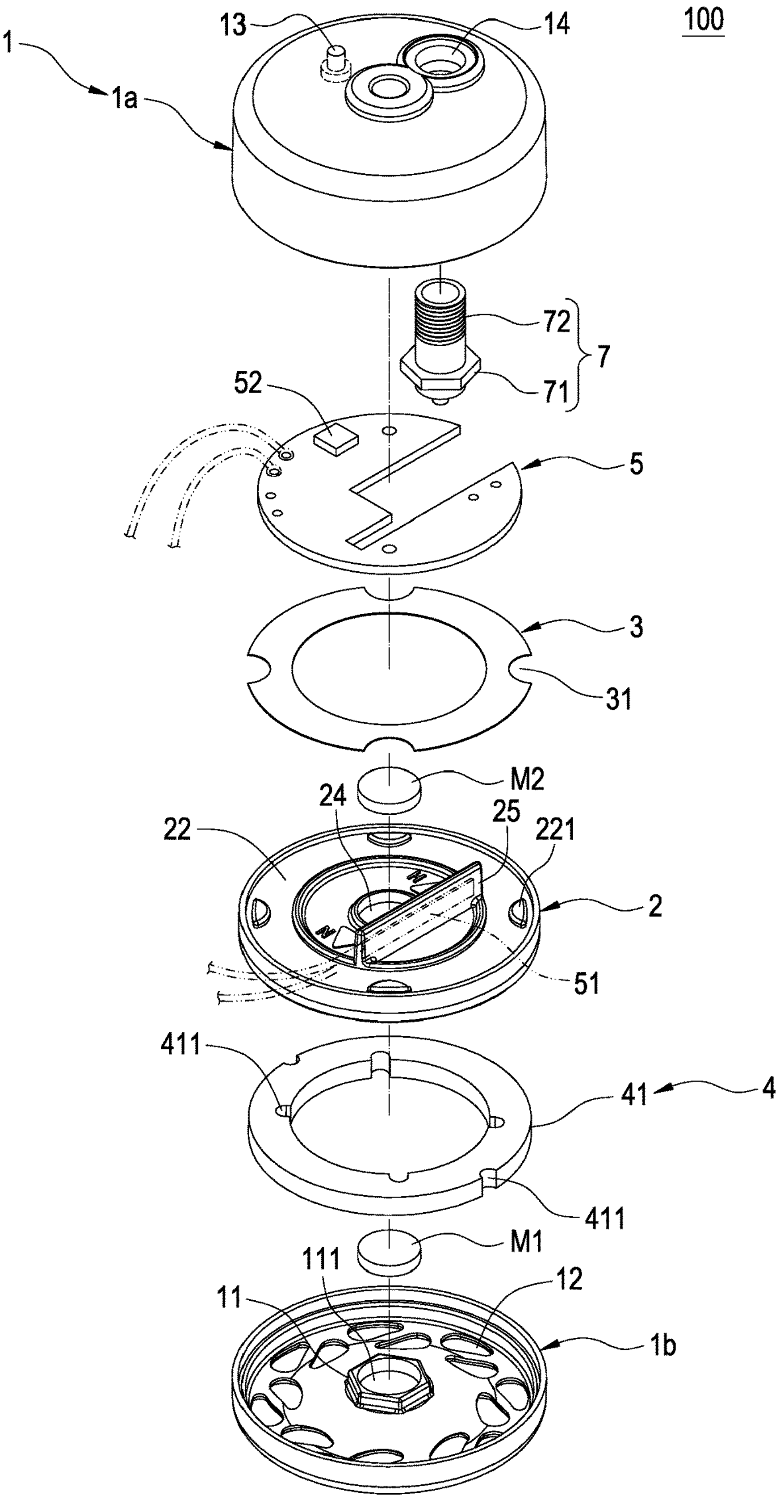
FIG. 1 is a perspective exploded view showing an essential oil volatilizing structure from a top view according to the present disclosure.

Please refer to FIG. 1 and FIG. 2, for positioning the essential oil unit 4 and the heating unit 3 on the heat conducting unit 2, the outer surface and the inner surface of the heat conducting unit 2 are concavely formed with a first positioning slot 21 and a second positioning slot 22. In some embodiments, the first positioning slot 21 is convexly formed with a plurality of first positioning members 211 and the second positioning slot 22 is convexly formed with a plurality of second positioning members 221, the essential oil carrying member 41 of the essential oil unit 4 is correspondingly formed with a plurality of first positioning parts 411 and the heating unit 3 is correspondingly formed with a plurality of second positioning parts 31.

Accordingly, the essential oil unit 4 and the heating unit 3 may be respectively disposed in the first positioning slot 21 and the second positioning slot 22. The essential oil unit 4 and the heating unit 3 are respectively positioned in the first positioning slot 21 and the second positioning slot 22 through each of the first positioning members 211 being latched with each of the first positioning parts 411 and each of the second positioning members 221 being latched with each of the second positioning parts 31.

Please refer from FIG. 1 to FIG. 5, for allowing the liquid-state essential oil to easily be replenished (or being replaced with a solid-state essential oil), the air permeable cover 1*b* of the housing 1 may be easily detached.

Details are provided as follows. The air permeable cover 1*b* has a first magnetic attracting member M1, the heat conducting unit 2 may be a member capable of being magnetically attracted by the first magnetic attracting member M1, and the heat conducting unit 2 is exposed on the seat opening of the seat member 1*a*. As such, the first magnetic attracting member M1 is magnetically adhered on the outer surface of the heat conducting unit 2 via the magnetism of the first magnetic attracting member M1, as long as the air permeable cover 1*b* is close to the heat conducting unit 2, and the essential oil unit 4 may be covered in the housing 1 via the air permeable cover 1*b*. On the other hand, the air permeable cover 1*b* may be detached when an external force is applied.

In some embodiments, the heat conducting unit 2 is a metal heat conducting unit (for example a heat conducting unit made of copper) having a desirable heat conductibility, a second magnetic attracting member M2 is disposed on the inner surface of the heat conducting unit 2, thus the first magnetic attracting member M1 and the second magnetic attracting member M2 are magnetically attracted while being partitioned by the heat conducting unit 2, and the essential oil unit 4 may be covered in the housing 1 via the air permeable cover 1*b*. On the other hand, the air permeable cover 1*b* may be detached when an external force is applied. In some embodiments which are not shown in figures, the second magnetic attracting member M2 may be disposed on the outer surface of the heat conducting unit 2, and the first magnetic attracting member M1 may be directly and magnetically attracted with the second magnetic attracting member M2.

Please refer from FIG. 1 to FIG. 5, for preventing the air permeable cover 1*b* and the heat conducting unit 2 from relatively rotating, an anti-rotating component 11 in non-circular shape is convexly disposed on an inner surface of the air permeable cover 1*b*, a corresponding anti-rotating component 23 is disposed on the outer surface of the heat conducting unit 2, and the corresponding anti-rotating component 23 has a corresponding recessed part 231 corresponding to the anti-rotating component 11 and formed in the same non-circular shape. In some embodiments, the non-circular shape may be any geometric shape having at least one linear side, for example a semicircular shape, a triangular shape, a rectangular shape or a polygonal shape having equal to or more than five sides. As such, when the user uses the air permeable cover 1*b* to cover, the anti-rotating component 11 is correspondingly mounted in the corresponding recessed part 231, a linear side of the anti-rotating component 11 and a linear side of the corresponding recessed part 231 are aligned to be adjacent to each other, thus the air permeable cover 1*b* and the heat conducting unit 2 are prevented from relatively rotating.

In some embodiments, for effectively using the space, the anti-rotating component 11 is further concavely formed with a first accommodation slot 111, and the first magnetic attracting member M1 is embedded in the first accommodation slot 111. A second accommodation slot 24 is concavely formed on the inner surface of the heat conducting unit 2, and the second magnetic attracting member M2 is embedded in the second accommodation slot 24. As such, effects of not occupying additional space and positioning the first magnetic attracting member M1 and the second magnetic attracting member M2 are achieved.

Please refer from FIG. 1 to FIG. 4, for reacting or instantly reacting a heating temperature of the heating unit 3 to the heat conducting unit 2, the electric circuit board 5 is electrically connected to a heat sensing unit 51 and a reacting unit 52. The present disclosure is not intended to be limiting to the electrical connecting means. For example, the reacting unit 52 is electrically disposed on the electric circuit board 5, and the heat sensing unit 51 is connected to the electric circuit board 5 by utilizing a transmission cable (not labeled). The heat sensing unit 51 is used for sensing a heating temperature of the heating unit 3 to the heat conducting unit 2, and the reacting unit 52 is used for reacting or instantly reacting to the temperature sensed by the heat sensing unit 51.

The heat sensing unit 51 may be disposed at any desired part of the heat conducting unit 2, as long as the heating temperature of the heating unit 3 to the heat conducting unit 2 may be sensed. In some embodiments, the heat conducting unit 2 further has a heat sensing part 25 (a heat sensing part integrally extended to be in a protruded status). The heat sensing unit 51 is disposed on the heat sensing part 25, thus the heating temperature of the heating unit 3 to the heat conducting unit 2 is sensed by the heat sensing unit 51 via the heat sensing part 25. The reacting unit 25 may be a sound generating unit (not shown in figures) or a light emitting unit as shown in figures, and the light emitting unit emits light with a corresponding preset color according to a temperature sensing range sensed by the heat sensing unit 51. In some embodiments, a light guiding unit 13 is embedded in the seat member 1*a*, the light guiding unit 13 is used for increasing a brightness of the light emitted from the light emitting unit and guiding the light of the light emitting unit to the exterior of the housing 1.

Moreover, please refer to FIG. 1, FIG. 2, FIG. 4, FIG. 6, FIG. 7 and FIG. 8, the essential oil volatilizing structure 100 disposed in the negative-pressure cup 900 includes a fastening column 7 and a fastening unit 8. A cup bottom (not labeled) of the negative-pressure cup 900 have a plurality of penetrated holes 9.

A base (not labeled) of the seat member 1*a* has a fastening hole 14, and the seat member 1*a* is disposed with a first corresponding fastening part 15 (as shown in FIG. 4) at a location corresponding to the fastening hole 14.

The fastening column 7 has two end parts, and the two end parts are respectively defined as a first fastening part 71 and a second fastening part 72. The first fastening part 71 is a polygonal sheet member protruded from a columnar body (not labeled) of the fastening column 7, and the second fastening part 72 is an outer thread formed on an outer circumferential wall of the columnar body, but here is not intended to be limiting.

The fastening unit 8 has a second corresponding fastening part 81, and the second corresponding fastening part 81 and the second fastening part 72 are mutually fastened. The fastening unit 8 may be any component capable of being correspondingly fastened with the second fastening part 72. In some embodiments, a screw nut is adopted as an example for illustrations, as such, the second corresponding fastening part 81 may be an inner thread formed on an inner circumferential wall of the fastening unit 8, thus the second fastening part 72 is threaded with the second corresponding fastening part 81.

The first fastening part 71 of the fastening column 7 is fastened with the first corresponding fastening part 15 of the housing 1, and a protruded portion (shown in FIG. 4 and not labeled, and the protruded portion includes the second fastening part 72) of the fastening column 7 is formed through protruding out from the housing 1 through the fastening hole 14. The essential oil volatilizing structure 100 is disposed in the negative-pressure cup 900, and the protruded portion of the fastening column 7 protrudes out the negative-pressure cup 900 from one of the penetrated holes 9 of the negative-pressure cup 900 to make the second fastening part 72 be exposed. Lastly, the second corresponding fastening part 81 of the fastening unit 8 is threaded with the second fastening part 72 of the fastening column 7, thus the base of the housing 1 and the cup bottom of the negative-pressure cup 900 are clamped between the first fastening part 71 and the fastening unit 8 for a purpose of being fastened.

Accordingly, the essential oil volatilizing structure 100 is disposed in the negative-pressure cup 900, and the air permeable cover 1*b* used for outputting gaseous-state essential oil may face the uncomfortable part of the person having the massaging treatment.

While this disclosure has been described by means of specific embodiments, numerous modifications and variations could be made thereto by those skilled in the art without departing from the scope and spirit of this disclosure set forth in the claims.

What is claimed is:

1. A negative-pressure massaging device, comprising:
a negative-pressure cup; and
an essential oil volatilizing structure, disposed in the negative-pressure cup and comprising:
a heat conducting unit;
a heater, disposed on and contacting the heat conducting unit to heat the heat conducting unit; and
an essential oil unit, disposed on and contacting the heat conducting unit to be heated;
wherein, the essential oil unit is heated by the heat conducting unit to volatilize an essential oil into the negative-pressure cup.

2. The negative-pressure massaging device according to claim 1, wherein the essential oil unit comprises a solid-state essential oil.

3. The negative-pressure massaging device according to claim 1, wherein the essential oil unit comprises a liquid-state essential oil and an essential oil carrying member, the essential oil carrying member is disposed on the heat conducting unit to be heated, the liquid-state essential oil is being absorbed in the essential oil carrying member, and the liquid-state essential oil absorbed in the essential oil carrying member is heated by the heat conducting unit to be volatized into the negative-pressure cup.

4. The negative-pressure massaging device according to claim 3, wherein the essential oil carrying member comprises a cotton member.

5. The negative-pressure massaging device according to claim 1, wherein the essential oil volatilizing structure further comprises a housing, the heat conducting unit, the heater and the essential oil unit are disposed in the housing, the housing comprises a seat member and an air permeable cover, the heat conducting unit is fastened on the seat member, the air permeable cover comprises a magnet disposed thereon, the air permeable cover is magnetically adhered on the heat conducting unit via the magnet and detachably disposed on the seat member.

6. The negative-pressure massaging device according to claim 5, wherein the magnet disposed on the air permeable cover is a first magnet, the heat conducting unit comprises a second magnet disposed thereon, and the air permeable cover is disposed on the seat member through the first magnet and the second magnet being magnetically attracted with each other directly or indirectly.

7. The negative-pressure massaging device according to claim 5, wherein the air permeable cover comprises an anti-rotating component of non-circular shape, the anti-rotating component comprises an accommodation slot, the magnet is disposed in the accommodation slot, the heat conducting unit comprises a corresponding anti-rotating component, and the corresponding anti-rotating component comprises a corresponding recessed part corresponding to the anti-rotating component in a same non-circular shape, and the anti-rotating component is correspondingly mounted in the corresponding recessed part to prevent the air permeable cover and the heat conducting unit from relatively rotating.

8. The negative-pressure massaging device according to claim 1, wherein the essential oil volatilizing structure further comprises an electric circuit board, the electric circuit board is electrically connected to a heat sensor, a light emitting component and the heater, the heat sensoring unit is disposed on heat conducting unit, the heat sensor is configured to sense a heating temperature of the heater via the heat conducting unit, and the light emitting component is configured to react to a temperature sensed by the heat sensor.

9. The negative-pressure massaging device according to claim 8, wherein the heat conducting unit comprises a heat sensing part, the heat sensor is disposed on the heat sensing part, and the heat sensor is configured to sense the heating temperature of the heater via the heat sensing part.

10. The negative-pressure massaging device according to claim 8, wherein the light emitting component is configured to emit light with a corresponding preset light color according to a temperature range sensed by the heat sensor.

11. The negative-pressure massaging device according to claim 1, wherein the heat conducting unit comprises a positioning slot disposed concavely on one surface thereof, and the essential oil unit is mounted in the positioning slot.

12. The negative-pressure massaging device according to claim 11, wherein the heat conducting unit comprises a plurality of positioning members disposed convexly in the positioning slot, the essential oil unit correspondingly comprises a plurality of positioning parts, and the essential oil unit is positioned in the positioning slot through each of the positioning members being correspondingly latched with each of the positioning parts.

13. The negative-pressure massaging device according to claim 1, wherein the essential oil volatilizing structure further comprises a housing, a fastening column and a fastening unit, the heat conducting unit, the heater and the essential oil unit are disposed in the housing, the housing comprises a fastening hole disposed thereon, one end part of the fastening column is fastened on the housing, another end part of the fastening column protrudes out of the housing via the fastening hole and penetrates the negative-pressure cup to be exposed, the fastening unit is correspondingly connected to the another end part, and the housing and the negative-pressure cup are clamped and fastened between the one end part of the fastening column and the fastening unit.

* * * * *